(12) United States Patent
Niemann et al.

(10) Patent No.: US 9,377,402 B2
(45) Date of Patent: Jun. 28, 2016

(54) METHOD AND SENSOR UNIT FOR DETECTING A DEGREE OF WETTING OF A GLASS PANE

(71) Applicant: Hella KGaA Hueck & Co., Lippstadt (DE)

(72) Inventors: Thomas Niemann, Delmenhorst (DE); Carsten Thun, Bremen (DE)

(73) Assignee: HELLA KGaA HUECK & CO., Lippstadt (DE)

( * ) Notice: Subject to any disclaimer, the term of this patent is extended or adjusted under 35 U.S.C. 154(b) by 0 days.

(21) Appl. No.: 14/671,687

(22) Filed: Mar. 27, 2015

(65) Prior Publication Data
US 2015/0276595 A1    Oct. 1, 2015

(30) Foreign Application Priority Data

Mar. 27, 2014    (DE) .......................... 10 2014 004 451

(51) Int. Cl.
| | | |
|---|---|---|
| *G01N 21/55* | (2014.01) | |
| *G05B 5/00* | (2006.01) | |
| *G01N 21/86* | (2006.01) | |
| *G01N 21/552* | (2014.01) | |
| G01N 21/47 | (2006.01) | |
| B60S 1/08 | (2006.01) | |

(52) U.S. Cl.
CPC .............. *G01N 21/552* (2013.01); *B60S 1/087* (2013.01); *B60S 1/0837* (2013.01); *G01N 21/474* (2013.01); *B60S 1/0825* (2013.01); *G01N 2021/4769* (2013.01); *G01N 2021/4773* (2013.01); *G01N 2201/062* (2013.01)

(58) Field of Classification Search
CPC .................... G01N 21/552; G01N 2021/4773; G01N 2201/062; B60S 1/0825; B60S 1/0837; B60S 1/087

USPC ........................ 356/445; 318/483; 250/559.41
See application file for complete search history.

(56) References Cited

U.S. PATENT DOCUMENTS

| | | | | |
|---|---|---|---|---|
| 5,391,891 A | * | 2/1995 | Wiegleb | B60S 1/0822 |
| | | | | 250/227.25 |
| 6,118,383 A | * | 9/2000 | Hegyi | B60S 1/0818 |
| | | | | 15/DIG. 15 |
| 2004/0178760 A1 | * | 9/2004 | Kobayashi | B60S 1/0822 |
| | | | | 318/483 |
| 2011/0128543 A1 | | 6/2011 | Choi | |
| 2013/0024169 A1 | * | 1/2013 | Veerasamy | B32B 17/10036 |
| | | | | 703/2 |

FOREIGN PATENT DOCUMENTS

| | | |
|---|---|---|
| DE | 3532199 A1 | 3/1987 |
| DE | 4006174 C1 | 7/1991 |
| DE | 19530289 A1 | 2/1997 |

(Continued)

*Primary Examiner* — Tarifur Chowdhury
*Assistant Examiner* — Sunghee Y Gray
(74) *Attorney, Agent, or Firm* — Muncy, Geissler, Olds & Lowe, P.C.

(57) ABSTRACT

A method for detecting a degree of wetting of a glass pane, in particular a windscreen of a motor vehicle, is provided. A transmitter is arranged on the inside relative to a glass pane and emits electromagnetic waves, which are reflected according to the total reflection principle on the outer, from the transmitter's point of view the opposite surface of the glass pane, and which are received by a receiver arranged on the inside relative to the glass pane. Electromagnetic waves are emitted further from a transmitter. Waves pass through the glass pane and are scattered on particles or droplets in front of the glass pane and are received by a receiver arranged on the inside relative to the glass pane.

15 Claims, 2 Drawing Sheets

(56) References Cited

FOREIGN PATENT DOCUMENTS

| DE | 19746351 | A1 | 10/1998 |
| DE | 10311800 | A1 | 9/2004 |
| DE | 102004047215 | A1 | 4/2006 |
| DE | 10339696 | B4 | 12/2007 |
| DE | 102007035905 | A1 | 2/2009 |
| EP | 1306276 | B1 | 11/2005 |

\* cited by examiner

METHOD AND SENSOR UNIT FOR DETECTING A DEGREE OF WETTING OF A GLASS PANE

BACKGROUND OF THE INVENTION

1. Field of the Invention

The invention relates to a method for detecting a degree of wetting of a glass pane, in particular a windscreen of a motor vehicle, where electromagnetic waves are emitted by a transmitter arranged on the inside relative to the glass pane, which are reflected according to the total reflection principle on the outer, from the transmitter's point of view the opposite surface of the glass pane, and which are received by a receiver arranged on the inside of the pane. Furthermore the invention relates to a sensor unit for detecting a degree of wetting of a glass pane, in particular a windscreen of a motor vehicle, with a transmitter arranged on the inside relative to the glass pane, which emits electromagnetic waves reflected according to the total reflection principle on the outer, from the transmitter's point of view the opposite surface of the pane, and with a receiver arranged on the inside relative to the pane, which receives the reflected electromagnetic waves.

2. Brief Discussion of the Related Art

Sensor units of this kind are known. Sensor means working according to the principle of total reflection are, for example, described in the DE 40 06 174 C1, the DE 197 46 351 A1, the DE 103 39 696 B4 and the DE 35 32 199 A1.

Apart from sensor units working according to the total reflection principle there are sensor units which operate with scattered light. Here electromagnetic waves are directed at as steep an angle as possible at the windscreen and penetrate the windscreen and are scattered on droplets, ice or other particles in front of the windscreen. The electromagnetic waves thus scattered are then received by a receiver arranged on the inside relative to the windscreen. Based on this evaluation conclusions can also be drawn as to the degree of wetting of the windscreen. Such a sensor unit has been described, for example, in the US 2011/0128543 A1.

Furthermore capacitive measuring methods are feasible, with which the degree of wetting of a glass pane may be measured. Such capacitive measuring methods have, for example, been described in the DE 10 2007 035 905 A1 and the EP 1 306 276 B1.

A generic publication is also known from the DE 103 11 800 A1. Further comparatively similar methods and devices are known from the DE 195 30 289 A1 and the DE 10 2004 047 215 A1.

SUMMARY OF THE INVENTION

The invention is based on the requirement to propose a method and a sensor unit of the kind mentioned in the beginning with which a particularly accurate and reliable detection of the degree of wetting of a glass pane is possible.

With a method for the detection of a degree of wetting of a glass pane, in particular a windscreen of a motor vehicle, comprising a transmitter arranged on the inside relative to a glass pane and emitting electromagnetic waves reflected according to the total reflection principle at the outer, from the transmitter's point of view the opposite surface of the glass pane, and which are received by a receiver arranged on the inside relative to the pane, provision is made furthermore, according to the invention, for electromagnetic waves to be emitted by a transmitter, which pass through the glass pane and are scattered on particles or drops in front of the glass pane and are received by a receiver, wherein the receiver is arranged between the transmitter operating according to the total reflection principle and the transmitter for scattered light measuring, and there receives the electromagnetic waves. Furthermore receipt of the electromagnetic waves by the receiver is effected close to the transmitter for scattered light measuring and at a distance more than twice as large to the transmitter which operates according to the total reflection principle.

According to the invention two different measuring methods are thus combined. This allows particularly good results to be achieved. For measurements with the total reflection principle it is possible to particularly well detect normal smaller droplets on the windscreen. For measurements with the scattered light principle it is possible to particularly well detect large amounts of water or sheets of ice which have accumulated on the glass pane.

Evaluation and determination of the degree of wetting of the glass pane is based on the results of both measuring methods, thus leading to an overall result with which the degree of wetting of a glass pane with rain and water droplets is particularly well detected.

With a preferred development of the method only a single receiver is used, which on the one hand receives electromagnetic waves reflected according to the total reflection principle and the other, receives electromagnetic waves reflected according to the scattered light principle. To this end a circuit is provided which switches between two different modes so that one and the same receiver on the one hand, receives measurements according to the total reflection principle and on the other, receives measurements according to the scattered light principle, followed by a respective evaluation. Preferably transmission of the electromagnetic waves of the two measuring principles is thus carried out alternately. In a first time period an electromagnetic wave, reflected according to the total reflection principle, is emitted by a transmitter, and in a second time period an electromagnetic wave reflected according to the scattered light principle is emitted by a transmitter. In this way it is ensured that the one or more receivers receive light reflected according to only one principle, thereby permitting an unequivocal evaluation to be effected. With an operation, where both measuring principles are run in parallel with two separate transmitters and two separate receivers, it is possible to either operate the transmitters alternately, or preferably to effect an optical separation so that it is ensured that each receiver receives only the electromagnetic waves emitted from its associated transmitter. Then the two transmitters and receivers can operate continuously.

In another preferred further development of the method provision is made additionally for capacitive measuring in order to detect the degree of wetting of a glass pane. Preferably the results of the two/three measuring principles are then evaluated in a single microcontroller. From the result thus obtained a signal for wiper control is derived. Information for the light and headlight settings can also be derived.

A further aspect of the invention consists in providing a sensor unit for the detection of a degree of wetting of a glass pane, in particular a windscreen of a motor vehicle, with a transmitter arranged on the inside relative to a glass pane, which is suited and configured to emit electromagnetic waves which are reflected according to the total reflection principle at the outer, from the transmitter's point of view the opposite surface of the glass pane, and with a receiver arranged on the inside relative to the pane, which receives the reflected electromagnetic waves. Such a sensor unit is characterised according to the invention in that this comprises a transmitter arranged on the inside relative to the pane, which is suited and configured to emit electromagnetic waves which pass through the pane and are scattered on particles in front of the pane, and which comprises a receiver arranged on the inside relative to a glass pane, which receives the scattered electromagnetic waves. The receiver is arranged between the transmitter which operates according to the total reflection principle and the transmitter for scattered light measuring. Further, the distance between the receiver and the transmitter which operates according to the total reflection principle, is more than twice as large as the distance between the receiver and the transmitter for scattered light measuring.

In this way a sensor unit is provided which is suited and configured with its respective transmitters and receivers, for measuring on the one hand, the degree of wetting on the surface of the glass pane according to the total reflection principle and on the other, for measuring the degree of wetting on the surface according to the scattered light principle. In particular droplet-shaped rain and droplet-shaped moisture can be particularly well measured with the transmitter and receiver which for transmitting and receiving the electromagnetic waves operate according to the total reflection principle. Layers of ice or completely closed moisture films or water films, i.e. a degree of wetting of 100%, can be particularly well detected according to the principle of scattered light detection.

In a particularly preferred embodiment of the invention the receiver for receiving the totally reflected electromagnetic waves is the same receiver which receives the scattered electromagnetic waves. In particular therefore this embodiment comprises one receiver and two separate transmitters, wherein those electromagnetic waves scattered on the outer side of the pane according to the total reflection principle, are emitted from one of them, and those electromagnetic waves incident at almost right angles on the pane and passing through it, are emitted from the other. To this end an evaluation circuit is preferably provided, which coordinates the transmitters and switches them alternately so that at a certain point in time the receiver receives only reflected or non-scattered electromagnetic radiation from respectively one transmitter, and the evaluation circuit detects from which one of the transmitters the received light is received at the receiver.

In a preferred development of the invention the sensor unit comprises an optics on the inside of the pane for bunching the electromagnetic waves scattered according to the total reflection principle.

Within the sensor unit the distance between the transmitter operating according to the total reflection principle and the receiver is larger, in particular more than twice as large and in particular three times as large as the distance between the transmitter operating according to the scattered light principle and the associated receiver.

In another preferred further development of the invention the sensor unit additionally comprises a capacitive sensor with which the degree of wetting is measured. Such a capacitive sensor comprises two electrically conducting surfaces which form the surfaces of a capacitor. The capacitance of the thus formed capacitor changes as a result of moisture on the glass pane and from the change in capacitance conclusions can be drawn in turn regarding the moisture.

Preferably the scattered light sensor, the total reflection sensor and the transmitter are accommodated within a common housing. It is favourable if provision is made for a wall inside the housing, which prevents that light coming from the transmitter for the total reflection directly reaches the receiver. Two optics are provided in the housing to take these measurements according to the total reflection principle. The wall is preferably arranged between these two optics.

BRIEF DESCRIPTION OF THE DRAWINGS

The invention will now be explained in more detail by way of an exemplary embodiment shown in the drawing, in which.

DETAILED DESCRIPTION OF THE PREFERRED EMBODIMENTS

Figure 1:
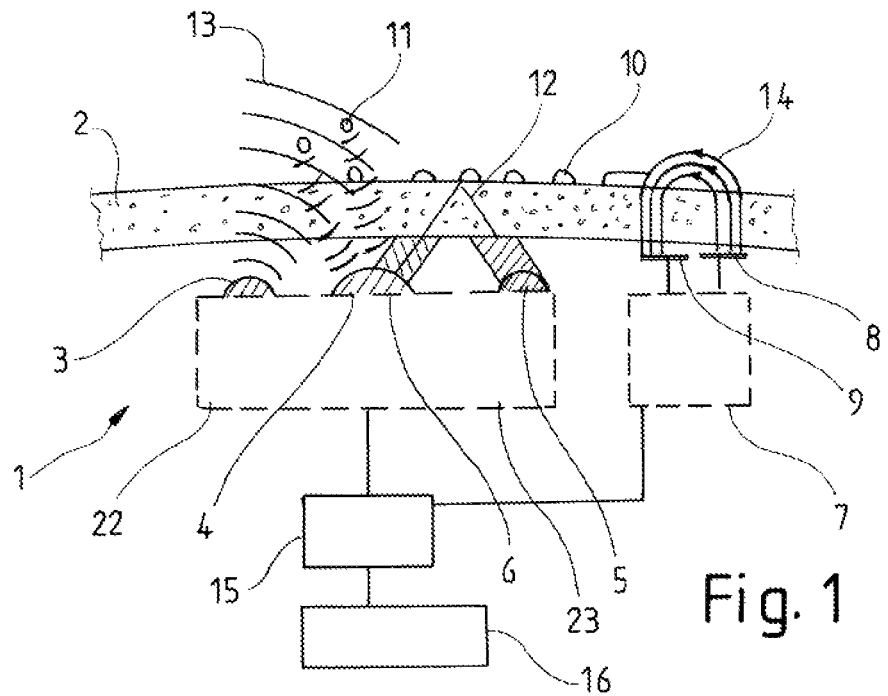
FIG. 1 shows a schematic illustration of a first embodiment of the invention.

FIG. 1 shows a first embodiment of the invention, where a device 1 for detecting a degree of wetting of a glass pane 2 is schematically illustrated. The device 1 is arranged on the inside relative to the glass pane 2, in particular a windscreen. Sensor units 1 of this kind are typically arranged on the glass pane 2 in the interior of motor vehicles. A first transmitter 3 is provided and configured for scattered light measuring and emits electromagnetic waves 13 for taking scattered light measurements. These are directed at the glass pane 2 at a comparatively steep angle and penetrate the same. The electromagnetic waves 13 are reflected from droplets 11 in the outside area of the glass pane 2. This outside area may also be characterised as an area, in which the sensor unit 1 with the transmitter 3 is arranged, which lies opposite the inside area or the area in which the sensor unit 1 with the transmitter 3 is arranged. The electromagnetic waves 13 reflected from the water droplets 11 are then received by a receiver 4 for scattered light measuring. The receiver 4 is provided and configured for receiving the reflected waves 13 after taking scattered light measurements. The radiation thus received and the signal thus obtained in the receiver 4 is evaluated by a microcontroller 15. The signal thus evaluated is used, for example in a wiper control 16. Furthermore a second transmitter 5 is provided in the sensor unit 1, which is configured for the emission of electromagnetic waves 12 which are totally reflected from the outer surface of the glass pane 2 and which are then received by an associated receiver 6 which is provided and configured for receiving electromagnetic waves 12 after total reflexion. If there exist water droplets 10 on the top of the glass pane 2 in the area of the totally reflected electromagnetic waves 12, part of the electromagnetic waves 12 is decoupled, and the intensity received by the receiver 6 decreases. In the embodiment illustrated here, the receiver 4 for scattered light measuring and the receiver 6 for taking measurements after total reflection are constructionally combined in a single receiver. The two transmitters 3 and 5 are switched alternately by the microcontroller 15 so that the receiver 4, 6 alternates between receiving the electromagnetic waves 13 emitted by the transmitter 3 and the electromagnetic waves 12 emitted by the transmitter 5. The electric signal generated in the receiver 4 is passed to the microcontroller 15 for further evaluation. The microcontroller 15 evaluates the electric signals of receiver 4 as a function of whether these are based on the electromagnetic waves emitted from the transmitter 3 or from the transmitter 5. From the obtained information a total information is ascertained which is used as a basis for activating the wiper control 16. Information may also be derived which is used for controlling the air conditioning or the lighting. Further a capacitive sensor 7 is provided in the sensor unit 1 of FIG. 1, which essentially comprises two capacitor surfaces 8 and 9 arranged on the inside of the glass pane 2. Field lines 14 form between these capacitor surfaces 8 and 9. The capacitance of the capacitor thus formed is also dependent on whether or not there are water droplets 10 on the glass pane 2. From the resulting change in capacitance conclusions can then be drawn on the presence of water. The measured results of the capacitive sensor 7 are also passed to the microcontroller 15 and evaluated there.

Figure 2:
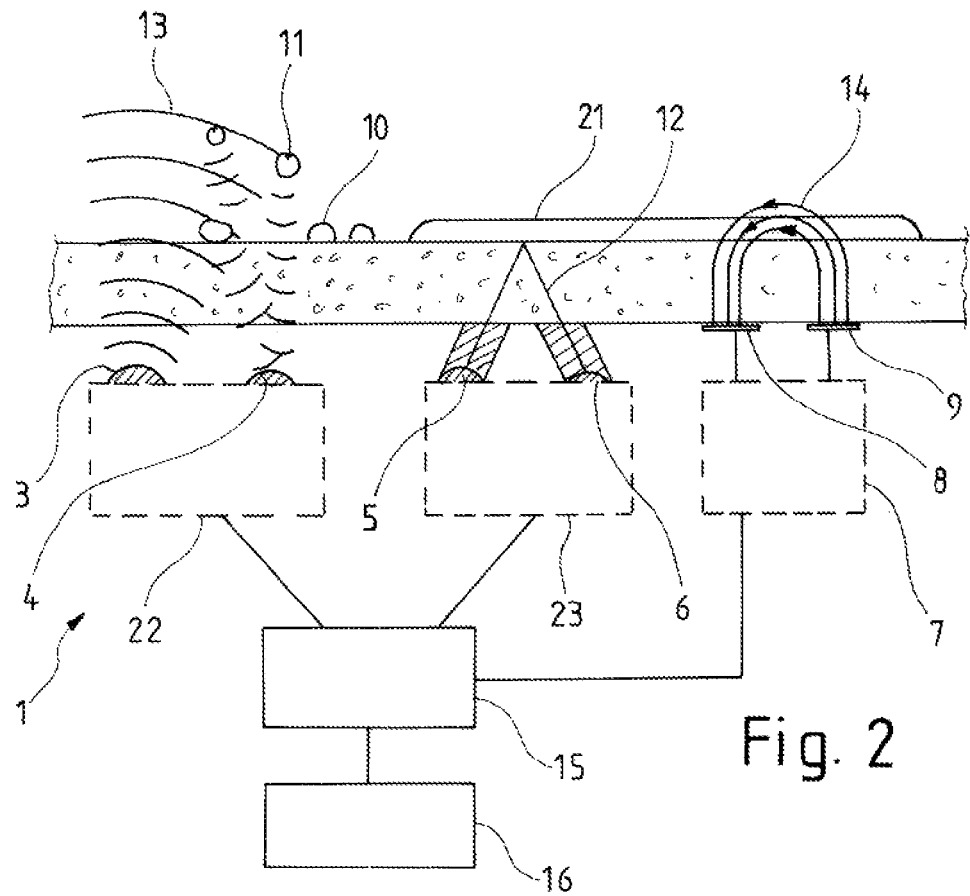
FIG. 2 shows a schematic illustration of a second embodiment of the invention.

FIG. 2 shows a second embodiment of the invention. Here the sensor unit 1 comprises three separate sensors, i.e. the scattered light sensor 22, the total reflection sensor 23 and the capacitive sensor 7. The scattered light sensor 22 here comprises a transmitter 3 for scattered light measuring and a receiver 4 for scattered light measuring. The transmitter 3 transmits the electromagnetic waves 13 which penetrate through the glass pane 2. These are directed comparatively steeply at the glass pane 2, so that this does not produce total reflection. The electromagnetic waves 13 are scattered on water droplets 11, in particular those which are still at a certain distance from the glass pane 2. Scattering and reflection also takes place on the water droplets 10 still adhering to the glass pane 2. The electromagnetic waves 13 which are scattered back are received by the receiver 4. In deviation from the embodiment as per FIG. 1 the total reflection sensor 23 here is configured with a transmitter 5 and its own receiver 6. Here too a capacitive sensor 7 is provided which again comprises capacitor surfaces 8 and 9. In particular with the total reflection sensor 23 the existence of a water film 21, such as indicated here, cannot be unequivocally identified. Precisely for such borderline situations the use of several sensors in a sensor unit 1 is favourable because it allows the strengths of the different sensors to be combined. The measured results of the capacitive sensor 7, the scattered light sensor 22 and the total reflection sensor 23 are evaluated in a microcontroller 15. The measurements taken by individual sensors are combined to form an overall result and this is used as a basis for operating the wiper control 16.

Figure 3:
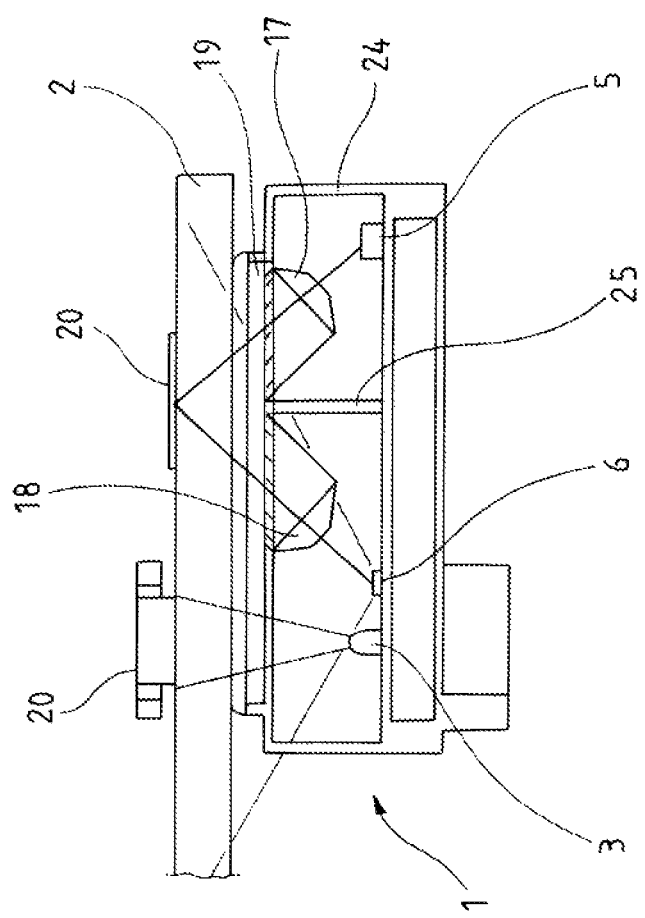
FIG. 3 shows a further embodiment of the invention.

FIG. 3 shows a concrete embodiment of a sensor unit 1. In this sensor unit 1 a scattered light sensor 22 and a total reflection sensor 23 are constructionally combined. Within a common housing 24, a transmitter 3, in particular a LED, is arranged on the floor of the housing 24 and thus at a distance from the glass pane 2. In comparative proximity to the transmitter 3 a receiver 4 is arranged also on the floor of the housing 24, which receives the scattered electromagnetic waves. In front of the glass pane 2 a sensitive area 20 is drawn, which indicates that not only water and other particles are detected directly on the glass pane 2, but also in a certain area in front of the same. A total reflection sensor 23 with a transmitter 5 is arranged in the housing 24. The transmitter 5 is also configured as a LED and is arranged on the floor of the housing 24. The transmitters 3 and 4 are arranged at opposite end areas of the housing 24. The transmitter 5 has an optics 17 assigned to it which is arranged on the ceiling of the housing 24, which again is directly facing the glass pane 2. In this way the light or the electromagnetic radiation coming from the transmitter 5, in particular in the infrared range, is focussed and directed at the glass pane 2 at a comparatively flat angle so that as a result, total reflection is obtained on the outer side of the glass pane 2 which faces the external environment. If in this area water and other particles are present on the glass pane 2, a part of that is decoupled, total reflection is not achieved and only a smaller part of the electromagnetic waves is reflected. A sensitive area 20 here is marked with 20. This indicates that the sensitive area 20 here is distinctly flatter than the other sensitive area 20 which is created during scattered light measuring. A further optics 18, which is assigned to a receiver 6, is also arranged on the ceiling of the housing 24 and focusses the totally reflected electromagnetic wave in direction of the receiver 6. This receiver 6 is, in this case, identical to the receiver 4 for scattered light measuring. The receiver 4, 6 alternates between detecting light emitted by the transmitter 3 from scattered light measuring and detecting light emitted by the transmitter 5 for measuring according to the total reflection principle. Furthermore a wall 25 is provided in the housing 24, which is arranged between the optics 17 and 18 and which prevents light from the transmitter 5 reaching the receiver 6 by the direct route. The distance between the receiver 4, 6 and the transmitter 3 is distinctly smaller than the distance between the receiver 4, 6 and the transmitter 5.

All features named in the above description and the claims can be selectively randomly combined with the features of the independent claim. The disclosure of the invention is therefore not limited to the described/claimed feature combinations, rather all feature combinations meaningful in terms of the invention are to be considered as disclosed.

The invention claimed is:

1. A method for detecting a degree of wetting of a glass pane, with a first transmitter that is arranged on the inside relative to the glass pane and that emits first electromagnetic waves from the first transmitter's point of view to the opposite surface of the glass pane, the first electromagnetic waves emitted from the first transmitter being reflected at an outer surface of the glass pane according to the total reflection principle, and received by a receiver which is arranged on the inside relative to the glass pane, wherein:
   second electromagnetic waves are emitted from a second transmitter, which pass through the glass pane and are scattered on particles or droplets in front of the glass pane and are received by the same receiver which is arranged on the inside relative to the glass pane,
   the receiver is arranged between the first transmitter working according to the total reflection principle and the second transmitter for scattered light measuring, and there receives the reflected electromagnetic wave and scattered electromagnetic wave, and
   a first distance between the first transmitter and the receiver is at least twice longer than a second distance between the second transmitter and the receiver.

2. The method according to claim 1, wherein the receiver switches between two different modes for receiving the first and second electromagnetic waves, respectively.

3. The method according to claim 1, wherein the second transmitter, which emits the second electromagnetic waves for scattered light measuring and the first transmitter, which emits the first electromagnetic waves according to the total reflection principle, transmit alternately.

4. The method according to claim 1, wherein capacitive measuring for determining the degree of wetting of the glass pane is performed with the aid of a capacitive sensor.

5. The method according to claim 1, wherein a results of various measurements are evaluated with an overall result being formed therefrom.

6. The method according to claim 1, wherein the glass pane is a windscreen of a motor vehicle.

7. A sensor unit for detecting a degree of wetting of a glass pane, comprising:
   a first transmitter that is arranged on the inside relative to the glass pane, and that first emits electromagnetic waves from the first transmitter's point of view to the opposite surface of the glass pane, the first electromagnetic waves emitted from the first transmitter being reflected according to the total reflection principle at the outer;

a receiver that is arranged on the inside relative to the glass pane, and that receives the reflected first electromagnetic waves; and a second transmitter that is arranged on the inside relative to the glass pane and that is suited and configured to emit second electromagnetic waves, which pass through the glass pane and are scattered on particles or droplets in front of the glass pane, the scattered second electromagnetic waves being received by the same receiver, wherein the receiver is arranged between the first transmitter working according to the total reflection principle and the second transmitter for scattered light measuring, and a first distance between the receiver and the first transmitter working according to the total reflection principle is at least twice longer than a second distance between the receiver and the second transmitter for scattered light measuring.

8. The sensor unit according to claim 7, wherein an evaluation circuit is provided which coordinates the first and second transmitters and switches them alternately, so that at a certain point in time the receiver exclusively receives either the second electromagnetic waves emitted by the second transmitter or exclusively receives the its electromagnetic waves reflected according to the total reflection principle.

9. The sensor unit according to claim 7, wherein the sensor unit comprises a capacitive sensor comprising two capacitor surfaces which are arranged on the inside on the glass pane.

10. The sensor unit according to claim 7, wherein the first distance between the receiver and the first transmitter is at least three times longer than the second distance between the receiver and the second transmitter for scattered light measuring.

11. The sensor unit according to claim 7, wherein the first transmitter which works according to the total reflection principle and the receiver each have an optics assigned to it.

12. The sensor unit according to claim 7, wherein the receiver and the first and second transmitters are arranged inside a common housing.

13. The sensor unit according to claim 12, wherein a partition is arranged in the housing which is arranged between two optics and prevents light coming from the first transmitter reaching the receiver by the direct route.

14. The sensor unit according to claim 7, wherein the glass pane is a windscreen of a motor vehicle.

15. A sensor unit for detecting a degree of wetting of a glass pane, comprising:
   a first transmitter that is arranged on the inside relative to the glass pane, and that first emits electromagnetic waves from the first transmitter's point of view to the opposite surface of the glass pane, the first electromagnetic waves emitted from the first transmitter being reflected according to the total reflection principle at the outer;
   a receiver that is arranged on the inside relative to the glass pane, and that receives the reflected first electromagnetic waves; and
   a second transmitter that is arranged on the inside relative to the glass pane and that is suited and configured to emit second electromagnetic waves, which pass through the glass pane and are scattered on particles or droplets in front of the glass pane, the scattered second electromagnetic waves being received by the same receiver,
   wherein the receiver is arranged between the first transmitter working according to the total reflection principle and the second transmitter for scattered light measuring,
   a first distance between the receiver and the first transmitter working according to the total reflection principle is at least twice longer than a second distance between the receiver and the second transmitter for scattered light measuring,
   wherein the receiver and the first and second transmitters are arranged inside a common housing, and
   a partition is arranged in the housing which is arranged between two optics and extends from a top surface to a bottom surface of the housing, thereby preventing light emitted from the first transmitter being directly received by the receiver.

* * * * *